US006790825B2

(12) United States Patent
Beck et al.

(10) Patent No.: US 6,790,825 B2
(45) Date of Patent: *Sep. 14, 2004

(54) METHOD OF USING SECRETIN AND COMPOSITIONS MADE THEREFROM FOR THE TREATMENT OF AUTISM AND OTHER NEUROLOGICAL, BEHAVIORAL AND IMMUNOLOGICAL DISORDERS

(75) Inventors: Victoria Beck, Bedford, NH (US); Bernard Rimland, San Diego, CA (US)

(73) Assignee: Repligen Corporation, Waltham, MA (US)

(*) Notice: Subject to any disclaimer, the term of this patent is extended or adjusted under 35 U.S.C. 154(b) by 99 days.

This patent is subject to a terminal disclaimer.

(21) Appl. No.: 09/800,431

(22) Filed: Mar. 5, 2001

(65) Prior Publication Data

US 2001/0049353 A1 Dec. 6, 2001

Related U.S. Application Data

(63) Continuation of application No. 09/229,208, filed on Jan. 13, 1999, now Pat. No. 6,197,746, and a continuation-in-part of application No. 09/080,631, filed on May 19, 1998, now Pat. No. 6,020,310.
(60) Provisional application No. 60/088,575, filed on Jun. 9, 1998, and provisional application No. 60/047,049, filed on May 19, 1997.

(51) Int. Cl.$^7$ .............................................. A61K 38/00
(52) U.S. Cl. .............................. 514/2; 514/12; 514/21; 424/184.1; 424/198.1; 530/300; 530/324; 436/86; 436/87
(58) Field of Search ................................. 514/2, 12, 21; 424/184.1, 198.1; 530/300, 324; 436/86, 87

(56) References Cited

U.S. PATENT DOCUMENTS

| | | |
|---|---|---|
| 3,833,722 A | 9/1974 | Graybill et al. |
| 3,940,480 A | 2/1976 | Seunaga |
| 3,987,014 A | 10/1976 | Guiducci |
| 4,086,220 A | 4/1978 | Schlatter |
| 4,098,779 A | 7/1978 | König |
| 4,302,448 A | 11/1981 | Bickel |
| 4,462,991 A | 7/1984 | Higuchi et al. |
| 4,533,494 A | 8/1985 | Uchiyama |
| 4,711,847 A | 12/1987 | König |
| 4,778,794 A | 10/1988 | Naruse et al. |
| 4,806,336 A | 2/1989 | Carlquist et al. |
| 4,920,122 A | 4/1990 | Naruse et al. |
| 4,994,467 A | 2/1991 | Zimmerman |
| 5,008,251 A | 4/1991 | Gruber |
| 5,094,837 A | 3/1992 | Bis |
| 5,225,407 A | 7/1993 | Oakley et al. |
| 5,380,872 A | 1/1995 | Sugg et al. |
| 5,527,825 A | 6/1996 | Karson et al. |
| 5,686,311 A | 11/1997 | Shaw |
| 6,020,310 A | * 2/2000 | Beck et al. |
| 6,197,746 B1 | * 3/2001 | Beck et al. |

FOREIGN PATENT DOCUMENTS

| | | |
|---|---|---|
| WO | WO 94/16756 | 4/1994 |
| WO | WO/96/06635 | 7/1996 |
| WO | WO/98/52593 | 11/1998 |
| WO | 99/13061 | 12/1999 |

OTHER PUBLICATIONS

Horvath et al. 1998, J. of the Assoc. for Academic Minority Physicians, Jan., vol. 9, No. 1: 9–15 (see p. 10).*
Horvath et al., "Secretin Therapy—The Child Psychologist", *Journal of the Association for Academic Minority Physicians*, 9(1):9–15, (1998). Retrieved from the Internet: URL:http//www.childpsychology, com/autism/secretin.htm.
McShane, "Secretin in Autism", Autism Society of Alabama, Retrieved from the Internet URL:http://www.autism/alabama.org/secretin2.htm. (Dec. 1998).
Perry et al., "Secretin in Autism", *Journal of Child and Adolescent Psychopharmacology*, 8:247–248, (1998).
Willimann et al., "Lecithin Organogel as Matrix for Transdermal Transport of Drugs", *Journal of Pharmaceutical Sciences*, 81:871–874, (1992).
Conn's Current Therapy, Robert E. Paxkel Editor, p. 452 W.B. Saunders Co. Philadelphia PA, 1989.
Stedman's Medical Dictionary, 26$^{th}$ ed., Williams & Wilkins, Baltimore, MD p. 486, 1995.
Cook et al., "The Serotonin System In Autism", *Current Opinion in Pediatrics*, 8:348–354, (1996).
Harteveld et al., "Autism—Role of Drug Treatment and a Guide to its Use", *CNS Drugs*, 8(3):227–236, (1997).
Horvath et al., "Improved Social and Language Skills After Secretin Administration in Patients with Autistic Spectrum Disorders", *J. Assoc. Acad. Minority Physicians*, 9(1):9–15, (1998).

(List continued on next page.)

Primary Examiner—Christopher R. Tate
Assistant Examiner—B. Dell Chism
(74) Attorney, Agent, or Firm—Fish & Richardson P.C.

(57) ABSTRACT

Secretin and secretin compositions are used for the treatment of autism and other neurological, behavioral and immunological disorders. The method includes administering an effective amount of secretin, such as Secretin-Ferring, to a patient. In one example, 2 clinical units (CU) of Secretin-Ferring was dissolved in a 7.5 ml solution of sodium chloride and was intravenously injected over 1 minute. In another example, secretin was administered transdermally by applying dimethyl sulfoxide (DMSO) to the patients skin and rubbing about 15 CU of Secretin-Ferring into the DMSO. Other methods and compositions for administering the effective amount of secretin include other transdermal carrier substances, such as gels, lotions, or patches; oral carriers, such as tablets, capsules, or lozenges; inhalation through the nose or mouth (e.g., as an aerosol); suppository forms of secretin and secretin compositions; and using acoustic waves to cause the secretin to penetrate the skin.

24 Claims, No Drawings

OTHER PUBLICATIONS

Piven, "The Biological Basis of Autism", *Curr. Op. Neurobiol.*, 7:708–712, (1997).

Rapin et al., "Neurobiology of Autism", *Annals of Neurology*, 43:7–14, (1998).

Ritvo et al., "A Medical Model of Autism:Etiology, Pathology and Treatment", *Pediatric Annals*, 13(4):298–305,(1984).

Wickelgren, "Tracking Insulin to the Mind", *Science*, 280:517–518, (1998).

Wing, "The Autistic Spectrum", *The Lancet*, 350:1761–66, (1997).

Beck, "Transdermal Secretin and Our Approach," (letter to www.healthboards.com/autism/1089.html) SECRETIN-TALK@ONELIST.COM (Dec. 30, 1998).

Schopler et al., "Toward Objective Classification of Childhood Autism: Childhood Autism Rating Scale (CARS)", *J. of Autism & Dev. Disorders* 10(1) (1980) pp. 91–103.

Karelson et al., "Regulation of Adenylate Cyclase by Galanin, Neuropeitide Y, Secretin and Vasoactive Intestinal Polypeptide in Rat Frontal Cortex, Hippocampus and Hypothalamus", *Neuropeptides* 28; (1995) pp. 21–28.

vanCalker et al., "Regulation by secretin, vasoactive intestinal peptide, and somatostatin of cyclic AMP accumulation in cultured brain cells", *Proc. Natl. Acad. Sci. USA* 77(11), pp. 6907–6911 (1980).

McGill et al., "Secretin activates C1 channels in bile duct epithelial cells through a camp–dependent mechanism",*Am. J. Physiology*, 1994; 266:C731–6.

Leiter et al., "Secretin", *Gut peptides: Biochemistry and Physiology* edited by Walsh and Dockray, Raven Press, Ltd., New York, 1994: 147–93.

Fara et al., "Effect of secretin and cholecystokinin on small intestinal blood flow distribution",*Am. J. Physiology*, 1975; 229(5):1365–70.

Dollinger et al., "Effects of Secreting and Cholecystokinin on Motor Activity of Human Jejunum", *Digestion* 12:1975, pp. 9–16.

Horvath et al., "Improved social and language skills after secretin administration in patients with autistic spectrum disorders", *J. Assoc. for Academic Minority Physicians* 9(1):1998, pp. 9–15.

Raymond et al., "Hippocampus in autism: a Golgi analysis", *Acta Neuropathologica*, 1996 91(1):117–9.

Charlton et al., "Secretin immunoreactivity in rat and pig brain", *Peptides*, 1981; 2 suppl 1:45–9.

Fremeau et al., "Secretin stimulates cyclic AMP formation in the rat brain", *Journal of Neurochemistry*, 1986; 46(6):1947–55.

Fremeau et al., "Secretin: specific binding to rat brain membranes", *Journal of Neuroscience*, 1983; 3(8):162–05.

Kimura et al., "Effects of preoptic injections of gastrin, cholecystokinin, secretin, vasoactive intestinal peptide and PHI on the secretion of luteinizing hormone and prolactin in ovariectomized estrogen–primed rats", *Brain Research*, 1987; 410(2):315–22.

Bauman et al, "Histoanatomic observations of the brain in early infantile autism", *Neurology*, 1985; 35(6):866–74.

Minshew, "In vivo brain chemistry of autism", magnetic resonance spectroscopy studies in *The Neurobiology of Autism*, Bauman and Kemper (editors), The John Hopkins Press, Baltimore, 1994, 1994:66–85.

Bauman et al., "Neuroanatomic observations of the brain in autism" in *The Neurobiology of Autism*, Bauman and Kemper (editors), The John Hopkins Press, Baltimore, 1994, 1994:119–45.

Hoon et al., "The mesial–temporal lobe and autism: case report and review"[Review], *Developmental Medicine & Child Neurology*; 1992; 34(3):252–9.

Bachevalier et al., "The contribution of medial temporal lobe structures in infantile autism: a neurobehavioral study in primates", in *The Neurobiology of Autism*, Bauman and Kemper (editors), The Johns Hopkins Press, Baltimore, 1994, 1994:146–69.

Dawson et al., "Subgroups of autistic children based on social behavior display distinct patterns of brain activity", *Journal of Abnormal Child Psychology*, 1995; 23(5):569–83.

George et al., "Cerebral blood flow abnormalities in adults with infantile autism", *Journal of Nervous & Mental Disease*, 1992; 180(7):413–7.

Olsson et al., "Epilepsy in autism and autisticlike conditions: a population–based study", *Archives of Neurology*, 1988; 45(6):666–8.

Anderson et al., "Whole blood serotonin in autistic and normal subjects", *J. Child Psychology & Psychiatry & Allied Disciplines*, 1987; 28(6):885–900.

Garnier et al., "Dopamine–beta–hydroxylase (DBH) and homovanillic acid (HVA) in autistic children", *J. Autism & Developmental Disorders*, 1988; 16(1):23–9.

Bouvard et al., "Low–dose naltrexone effects on plasma chemistries and clinical symptoms in autism: a double–blind, placebo–controlled study", *Psychiatry Research*, 1995; 58(3):191–201.

El–Salhy et al., "Immunohistochemical evidence of gastro–entero–pancreatic neurhormonal peptides of vertebrate type in the nervous system of the larva of a dipteran insect, the Hoverfly, *Eristalis Aeneus*", *Regulatory Peptides* 1:1980, pp. 187–204.

McDougle et al., "Recent advances in the pharmacotherapy of autism and related conditions", *Child & Adolescent Psych. Clinics of N. Am.*, 1994; 3(1):71–89.

Patel et al., "Molecular cloning and expression of a human secretin receptor", *Molecular Pharmacology*, 1995; 47(3):467–73.

Lenzen et al., "Secretin stimulates bile ductular secretory activity through the camp system", *American Journal of Physiology*, 1992; 263(4 pt 1):G527–32.

Pollack et al., "Effect of secretin on growth of stomach, small intestine, and pancreas of developing rats", *Digestive Diseases & Sciences*, 1990; 35(6):749–58.

Lebenthal et al., "Immunoglobin concentrations in the duodenal fluids of infants and children" II. The Effect of pancreosymin and secretin. *Am. J. Gastroenterology*, 1981; 75(6):436–9.

Lawrence et al., "Effect of secretin on intestinal lymph flow and composition in the rat", *Quarterly J. Experimental Physiology*, 1981; 66(3):297–305.

Ohta et al., "Tissue–specific expression of the rat secretin precursor gene", *Biochemical & Biophysical Research Communications* 183(2):1982, pp. 390–395.

Itoh et al., "The secretin precursor gene: structure of the coding region and expression in the brain", *J. Biological Chemistry*, 1991; 266(19):12595–8.

Redgate et al., "Interaction of neuropeptides and biogenic amines on cyclic adenosine monophosphate accumulation in hypothalamic nuclei", *Brain Research*, 1986; 365(1): 61–9.

Usdin et al., "Two receptors for vasoactive intestinal polypeptide with similar specificity and complementary distributions", *Endocrinology*, 1994; 135(6):2662–80.

Beck, "Dateline," NBC television program, Oct. 7, 1998 (videotape available from Autism Research Institute, 4182 Adams Avenue, San Diego, CA 92116, www.autism.com/ari).

Beck, "Good Morning America" ABC television program, (videotape available from Autism Research Institute, 4182 Adams Avenue, San Diego, CA 92116, www.autism.com/ari)

Rimland, Autism Research Review International, Jan. 1999 Update, Autism Research Institute (www.autism.com/ari/secretin2.html) (Jan. 1999).

Rimland, "Secretin update: Dec. 1, 1998," Autism Research Review International, Autism Research Institute (www.autism.com/ari/secretin2.html) (Dec. 1, 1998).

Rimland, "1998 Year–End Letter," Autism Research Institute (www.autism.com/ari/yearend.html) (Nov. 30, 1998).

Binstock, Secretin, email to newsgroup bit.listserv.autism (Aug. 23, 1996).

Mayberry, Secretin, email to newsgroup bit.listserv.autism (Aug. 23, 1996).

Westland, Secretin, email to newsgroup bit.listserv.autism (Aug. 24, 1996).

Timpson, Secretin, email to newsgroup bit.listserv.autism (Aug. 24, 1996).

Conaty, Secretin, email to newsgroup bit.listserv.autism (Aug. 25, 1996).

Conaty, Pancreatic Lipase deficiency, email to newsgroup bit.listserv.autism (Aug. 26, 1996).

Mayberry, Secretin, email to newsgroup bit.listserv.autism (Sep. 10, 1996).

Mayberry, Canadian listmates, email to newsgroup bit.listserv.autism (Sep. 20, 1996).

Binstock, Secretin, email to newsgroup bit.listserv.autism (Sep. 26, 1996).

Mayberry, Peptide Hormone, Substance P, email to newsgroup bit.listserv.autism (Oct. 16, 1996).

Mayberry, Substance P/Seratonin/Secretin, email to newsgroup bit.listserv.autism (Jan. 27, 1997).

Mayberry, Measles and Substance P, email to newsgroup bit.listserv.autism (Feb. 10, 1997).

Hays, Digestion—CCK/Acetylcholine, email to newsgroup bit.listserv.autism (Mar. 27, 1997).

Westlund, Secretin, email to newsgroup bit.listserv.autism (Oct. 7, 1997).

Carlton, The Hypocretins: Hypothalamus–specific peptides, email to newsgroup bit.listserv.autism (Jan. 19, 1998).

Carlton, Dr. Shaw's Book arrived TODAY!, email to newsgroup bit.listserv.autism (Jan. 20, 1998).

Carlton, About Dr. Shaw's Book–Careful Venting Post!, email to newsgroup bit.listserv.autism (Jan. 21, 1998).

Carlton, Secretin "gushing", email to newsgroup bit.listserv.autism (Jan. 22, 1998).

Owens, Intestinal Hormones, email to newsgroup bit.listserv.autism (May 27, 1997).

Mayberry, Secretin Salve, email to newsgroup bit.listserv.autism (Jul. 17, 1997).

MJW28@aol.com (MJW28), Secretin, email to newsgroup bit.listserv.autism (Oct. 6, 1997).

* cited by examiner

METHOD OF USING SECRETIN AND COMPOSITIONS MADE THEREFROM FOR THE TREATMENT OF AUTISM AND OTHER NEUROLOGICAL, BEHAVIORAL AND IMMUNOLOGICAL DISORDERS

RELATED APPLICATION

This application is a continuation and claims the benefit of U.S. patent application Ser. No. 09/229,208, filed Jan. 13, 1999, now U.S. Pat. No. 6,197,746, which claims the benefit of U.S. Provisional Application Serial No. 60/088,575 filed Jun. 9, 1998, fully incorporated herein by reference, and is a continuation-in-part of U.S. patent application Ser. No. 09/080,631 filed May. 19, 1998 and entitled Method For Assisting in Differential Diagnosis And Treatment of Autistic Syndromes, now U.S. Pat. No. 6,020,310, which itself claims the benefit of United States Provisional Patent Application No. 60/047,049, filed May 19, 1997.

FIELD OF THE INVENTION

The present invention relates to methods and compositions for the treatment of neurological, behavioral and/or immunological disorders and more particularly, to a new medical use for the natural or synthetic hormone secretin in the treatment of autism and other neurological, behavioral and/or immunological disorders.

BACKGROUND OF THE INVENTION

Autism is a disabling neurological disorder that affects thousands of Americans and encompasses a number of subtypes, with various putative causes and few documented ameliorative treatments. The disorders of the autistic spectrum may be present at birth, or may have later onset, for example, at ages two or three. There are no clear cut biological markers for autism. Diagnosis of the disorder is made by considering the degree to which the child matches the behavioral syndrome, which is characterized by poor communicative abilities, peculiarities in social and cognitive capacities, and maladaptive behavioral patterns.

A number of different treatments for autism have been developed. Many of the treatments, however, address the symptoms of the disease, rather than the causes. For example, therapies ranging from psychoanalysis to psychopharmacology have been employed in the treatment of autism. Although some clinical symptoms may be lessened by these treatments, modest improvement, at best, has been demonstrated in a minor fraction of the cases. Only a small percentage of autistic persons become able to function as self-sufficient adults.

Although much controversy exists about the causes and treatments of autism, a few established biomedical findings have been made. Many individuals with autism experience intestinal difficulties, often including the inability to digest gluten and casein. Abnormalities have also been found in the metabolism of the neurotransmitter serotonin and in various parameters of immune system functions, for example, elevated Measles, Mumps and Rubella. (MMR) titers. Prior to the discovery of the present invention, however, no useful links had been made between these biomedical findings, nor had any Success treatments been derived therefrom, as disclosed in various articles incorporated herein by reference.[1]

[1] Priven, J. (1997). The biological basis of autism. *Current Opinion in Neurobiology*, 7, 708–712.
Rapin, L. & Katzman, R. (1998). Neurobiology of autism. *Ann Neurology*, 43, 7–14.

Similar to autistic spectrum disorder, many other behavioral, neurological and immunological disorders have been equally difficult to understand and to effectively treat. Such disorders include depression, obsessive-compulsive disorder, Alzheimer's, allergies, anorexia, schizophrenia, as well as other neurological conditions resulting from improper modulation of neurotransmitter levels or improper modulation of immune system functions, as well as behavioral disorders such as ADD (Attention Deficit Disorder) and ADHD (Attention Deficit Hyperactivity Disorder), for example. Accordingly, a need exists for a method and composition for the treatment of autism and other behavioral, neurological and/or immunological disorders.

The hormone secretin is a polypeptide hormone secreted by the mucosa of the duodenum and upper jejunum when acid chyme enters the intestine. The hormone secretin stimulates the pancreatic acinar cells to release bicarbonate and water, which are excreted into the duodenum and change the pH in the gut from acid to alkaline, thereby facilitating the action of digestive enzymes. Secretin is always used and indeed is intended only to be used in diagnostic tests given to patients with gastrointestinal disorders to stimulate the release of pancreatic juices for testing purposes.

Prior to the discovery of the present invention however secretin has never before been linked to autistic spectrum disorders, either as a possible cause or treatment, nor has it been used in the treatment of other neurological and/or immunological disorders, as herein proposed.

Wing, L. (1997). The autistic spectrum. *The Lancet*, 350 (December 13), 1761–1765.

SUMMARY OF THE INVENTION

The present invention features a method for the treatment of neurological, immunological and other disorders in a patient. The method comprises the step of stimulating the secretion of pancreatic juices in the patient. In one embodiment, stimulating the secretion of pancreatic juices comprises the step of administering to the patient an effective amount of natural or synthetic secretin. The preferred method of the present invention is for the treatment of autistic spectrum disorder.

According to one method of administering secretin, the secretin is administered by infusion and the effective amount is generally 2 clinical units (CU) per kilogram (kg) of body weight given intravenously within 1 minute. In another method, the secretin is administered transdermally by applying a transdermal carrier substance, such as dimethyl sulfoxide (DMSO) to the skin, applying crystalline secretin in an effective amount onto the carrier substance, and rubbing the composition into the skin. One example of an effective amount of secretin administered transdermally includes about 15 CU of crystalline secretin.

Other methods of administering secretin include, but are not limited to, administering secretin transdermally with a gel, lotion or patch; administering secretin with a suppository; administrating secretin orally, as tablet, capsule or lozenge; administrating secretin by inhalation (e.g., as an aerosol) either through the mouth or the nose; and administering secretin using acoustic waves to permeate the skin. The present invention also contemplates other physiologically acceptable carriers or excipients for carrying an effective amount of secretin into the patient's body.

In another embodiment, the method for stimulating the secretion of pancreatic juices comprises the step of causing the body to secrete secretin in an effective amount to at least ameliorate and preferably treat autism and other neurological and/or immunological disorders. This method includes, for example, stimulating or otherwise causing the duodenum and upper jejunum to secrete the hormone secretin for one or more of the purposes described herein.

The present invention also features compositions for use according to the above methods. In one embodiment, a pharmaceutical composition, according to the present invention includes an effective amount of secretin together with a suitable volume of sodium chloride for dissolving the secretin and carrying the secretin into the body by infusion. In another embodiment, a composition according to the present invention includes an effective amount of secretin and a transdermal carrier substance, such as DMSO for carrying the secretin into the body transdermally. Other compositions include an effective amount of secretin together with physiologically acceptable carriers or excipients for carrying the secretin into the patient's body. The present invention contemplates the use of both natural and synthetically produced secretin.

DETAILED DESCRIPTION OF THE PREFERRED EMBODIMENT

The present invention will be better understood from the following examples which are given by way of illustration and not by way of limitation. The patient, the same in both examples, is a boy with symptoms of autism. Although only two examples of treatment are presented on the same patient, the present invention has been tried on a number of children in accordance with the method of the first example with similar satisfactory results.

The patient in the present examples developed normally until about fourteen months of age, with the exception of gastrointestinal problems (i.e., chronic diarrhea and constipation) which began at about six months. At about thirteen months, when whole milk was introduced into his diet, the patient began having reoccurring ear infections. At about fourteen months, the patient appeared to lose the ability to process language, first receptively (at about 14 months) then expressively (at about 16 months). The patient also experienced episodes of "shivers" that appeared to be intermittent seizures.

After consulting with numerous neurologists, pediatricians, child development specialists, audiologists, endocrinologists, allergists, and other medical professionals, no consistent diagnosis had been reached. Although not clinically diagnosed with autism, the patient exhibits a number of behavioral symptoms of autism and pervasive developmental disorder (PDD) in general. The term autism is used herein for reference purposes only, and this invention is intended to apply to any number of pervasive developmental disorders as well as neurological and immunological disorders.

Prior to receiving the treatment with secretin, a single photon emission computed tomography (SPECT) scan of the brain revealed a decreased perfusion in the right hemisphere and left temporal lobe, with the most severe decrease in the right parietal occipital region. Also, steady state auditory evoked responses recorded in response to rapid amplitude and frequency modulations of a 1 kHz tone were abnormal, suggesting disturbances of neural mechanisms responsible for frequency and amplitude modulation analysis. Further, the patient's secretin cells prior to receiving treatment, measured at a level of 9, are far below the normal limit in the range of 20–70.

EXAMPLE 1

When the patient was three years old, the secretin was administered by way of an infusion as part of an upper gastrointestinal endoscopy. The secretin was used in this diagnostic procedure at the request of the patient's parents, one of which is an inventor of the present invention. The secretin used in this procedure is known as Secretin-Ferring available from Ferring Laboratories, Inc., Suffern, N.Y. (See Appendix A). The secretin was dissolved in a 7.5 solution of sodium chloride and administered in a dosage of 2 clinical units (CU) per kilogram (kg) body weight by intravenous injection over one minute. (I.E. 30 IU IV for approximately 15 kilograms of body weight.)

Immediately after the administration of the secretin, the diagnostic testing revealed that the patient's pancreas responded, quite surprisingly, with an unusually large amount of pancreatic juice being released (approximately 10 ml/min compared to a usual rate of 1–2 ml/min). The diagnostic tests performed on the patient during this procedure also indicated gastric inflammation. Within days after the administration of secretin, the patient's chronic abnormal bowel movements became normal, although no changes had been made in the patient's diet. Within weeks after the treatment, the patient was able to make normal eye contact, language appeared for the first time in two years, and other behavioral and developmental problems improved remarkably. The following Table I summarizes the improvements observed in the patient within 3 weeks after the infusion of secretin.

TABLE I

| Symptoms Before Secretin Infusion | Progress within 3 Weeks After the Secretin Infusion |
|---|---|
| Two words | 100's of words - will repeat some approximation of any work requested. |
| No sentences | Short sentences - such as; "I love you", "I want juice", "Good night mommy", "Thank you, daddy". |
| No flash cards | 40–50 flash cards. |
| No focus on requested tasks | Will sit and watch carefully. Will perform most tasks after watching once or twice. For instance, will sort by color or category. Will construct more complicated puzzles. Will respond appropriately to questions. |
| Diapers only | Completely potty trained. |
| Watch Videos | Now, gets "involved" interactively with his videos. He will imitate the hand motions, sing the songs or dance to the music. |
| Consistent sleeping problems. Although these were much worse when he was 18–24 months, prior to the procedure he was still up numerous times each night. | Has slept through almost every night entirely. |
| Infrequent (1–2 times/week) "spinning" episodes. | No spinning episodes. |
| Abnormal bowel movements | Normal bowel movements. |
| Excessive water consumption approximately 50 cups per day. | Excessive water consumption - no change approximately 50 cups per day. |
| Limited Diet Preferences (French Toast, bananas, French Fries, pancakes, crackers, cookies, raisins, chocolate, chicken nuggets.) | No Change |
| No apparent connections made between language and objects. | Many connections made between new language learned and objects. Recites names he has learned on flash cards when he sees the same on computer game or video. |
| No response to request for gestures. | Responds to all kinds of things such as, "blow a kiss", "Wave bye bye", etc. Will often now spontaneously say these things himself. |

TABLE I-continued

| Symptoms Before Secretin Infusion | Progress within 3 Weeks After the Secretin Infusion |
|---|---|
| No interest in drawing | Wants to draw constantly. Will draw complete face and name the parts as he draws. |
| Did not imitate commands. | Will imitate almost any multi-step command. |
| Minimal eye contact | Eye contact 75% of the time. |

Biomedical changes were also measured in the patient. A SPECT scan of the patient indicated that the perfusion of the right posterior parietal and right temporal lobes was improved. Blood tests taken after the treatment also indicated a rise in serotonin levels, and the patient's rubella titers dropped from 5.8 to 2.3.

Although the behavioral improvements continued, the rate of the patient's progress appeared to decrease at about 5 weeks. At the request of the patient's parents, a second infusion of secretin was performed about 9 months after the first infusion, and a third infusion of secretin was performed about three months after the second infusion. The second and third infusions of secretin achieved the same results in the patient.

EXAMPLE 2

At the time of this treatment, the patient was about 4 years old. Secretin was administered transdermally using pharmaceutical grade dimethyl sulfoxide (DMSO) (generally 99.9% pure) available from Clinic Service Co., Box 2512, Hemet Calif. 92543. The secretin (Secretin-Ferring) was administered daily in a dosage of about 75 CU over a five day period (i.e., about 15 CU daily). For each treatment, about 4 drops of DMSO were placed onto the skin of the patient, about 15 CU of the crystalline secretin was placed onto the DMSO, and the composition was rubbed into the skin.

The administration of secretin transdermally on a daily basis in this way has resulted in even more dramatic and significant improvements in the patient. Within a period of about 6 months, the patient has progressed to spontaneous and conversational language. When the daily dose of secretin is stopped, the autistic behavioral symptoms return.

It is important to note that similar results have been seen in numerous other autistic children using an intravenous administration of secretin in accordance with the teachings of the present invention, in order to validate the findings of the present invention.

Although the present invention is not limited by theory, it is believed that some autistic spectrum disorders are caused by a secretin deficiency resulting in a dysfunction of the pancreas. One function of the hormone secretin is to stimulate the pancreas to release bicarbonate and water, which change the pH in the gut from acid to alkaline, thereby facilitating the action of digestive enzymes. The gastrointestinal disorders, such as an inability to digest gluten and casein, in autistic patients is possibly caused by this failure of the pancreas to release enzymes.

One possibility is that abnormal opioid peptides in the gut create problems in the brain. These abnormal opioid peptides have been found to diminish on a casein free and gluten free diet. According to one study, autistic children that responded to this diet were given an infusion of secretin and the peptides were measured before and after the secretin infusion. After the secretin infusion, which stimulates the pancreas to release bicarbonate, the peptides disappeared.

The gastric inflammation observed in the patient in the above EXAMPLE 1 suggests that the improper pH resulting from this dysfunction of the pancreas may be a cause of the digestive problems and malabsorption of essential minerals and nutrients found in many individuals with autism. The unusual secretion by the pancreas in response to the secretin, as observed in EXAMPLE 1, further suggests that this dysfunction of the pancreas is caused by a secretin deficiency.

In addition to this effect on the digestive function, secretin also appears to improve the abnormal brain activity in individuals having symptoms of autism. The increased blood flow in the brain detected during a SPECT scan after administering secretin in EXAMPLE 1 supports this theory. While causing pancreatic secretions, secretin also stimulates the production of cholecystokinin (CCK). Deficiencies in CCK have been linked to other neurological disorders, such as schizophrenia, and CCK production has been found to be related to levels of the neurotransmitter serotonin. Thus, secretin may be indirectly related to the body's natural production of serotonin. The increase in serotonin levels in the blood after the procedure in EXAMPLE 1 supports this relationship between secretin and serotonin.

Without proper modulation of neurotransmitter levels (i.e., serotonin) in the brain, the brain will not function properly. The inability to modulate neurotransmitter levels has been found to be related to other neurological conditions as well as autism. Thus, a secretin deficiency may cause an imbalance or improper modulation of neurotransmitter levels that results in autistic spectrum disorder or other neurological disorders. Administering secretin to patients with these disorders will modulate the neurotransmitter levels and correct the behavioral symptoms, such as the inability to process language and other maladaptive behavioral patterns. The secretin may also correct abnormalities in immune system functions, as indicated by the reduction of measles, mumps and rubella antibodies in the patient after the secretin administration in EXAMPLE 1. Secretin has also been found to stimulate dopamine production through its precursor, tyrosine hydroxylase. Dopamine levels have been implicated in a variety of mental and behavioral disorders such as Parkinson's and Alzheimer's disease.

A secretin deficiency can therefore account for the gastrointestinal disorders as well as the behavioral symptoms found in many individuals with autistic spectrum disorder.

The therapeutic possibilities of the use of secretin appear to have been overlooked in the medical literature. For example, Guyton and Hall, in their widely used *Textbook of Medical Physiolocy* (9th edition, 1995–1997) mention briefly in passing that secretin can increase cellular utilization of insulin. Recent research suggests that insulin is required for normal brain functioning. (See also *Science* vol. 280 Apr. 24, 1998, p. 517–518). Furthermore, immunological disorders related to abnormally high levels of measles, mumps, and rubella (MMR) titers may also be treatable with secretin. Additionally, secretin is believed to stimulate antibodies to cows milk protein (and perhaps other proteins). Autism and other PDD's may be connected to protein intolerance and secretin may increase the body's tolerance to such protein(s). Secretin may also have histamine blocking capabilities.

Although the above examples use Secretin-Ferring, the present invention contemplates other forms of natural or synthetic secretin. The present invention also contemplates using other types of transdermal carrier substances in addition to DMSO. Further, the present invention contemplates other alternative ways of administering secretin including, but not limited to, administering secretin transdermally with a gel, lotion or patch; administering secretin with a suppository; administrating secretin orally, as tablet, capsule or lozenge; administrating secretin by inhalation (e.g., as an aerosol) either through the mouth or the nose. Such alternative methods of administering secretin are less invasive, do not have to be carried out by a doctor at a medical facility, and are less expensive. In addition, the level or dose of administration of secretin can be varied from those examples stated herein including, for example, intraveneous administration over a period of time of several hours instead of several minutes and/or a smaller, maintenance or daily dose administered intramuscularly, transdermally or by other methods as disclosed herein or their equivalent.

A further alternative method of transdermally administering secretin includes the use of acoustic waves to permeate the skin. For example, acoustic waves generated using ultrasound or a shockwave from a pulsed laser have been found to make the skin temporarily permeable. A few minutes of low-frequency ultrasound (sound greater in frequency than 20 kilohertz) creates tiny cavities through which the secretin (alone or combined with another transdermal carrier substance) can be diffused.

Accordingly, the method of treating autism by administering secretin and/or causing the body to naturally secrete required amounts of secretin corrects the secretin deficiency, improving the digestive functions in autistic patients previously experiencing intestinal difficulties and improving communication, cognition, and socialization capabilities of autistic patients. Since other neurological disorders, such as depression, obsessive-compulsive disorder, Alzheimer's, allergies, anorexia, bulimia, schizophrenia, also involve abnormal modulation of neurotransmitter levels, these disorders may also be treatable with secretin. Further, other disorders related to serotonin and dopamine may also be treatable with secretin.

Modifications and substitutions by one of ordinary skill in the art are considered to be within the scope of the present invention which is not to be limited except by the claims which follow.

What is claimed is:

1. A method for treating a patient exhibiting a symptom of autistic disorder comprising the step of stimulating secretion of pancreatic juices in said patient.

2. The method of claim 1 wherein the step of stimulating secretion of pancreatic juices comprises the step of administering to said patient an amount of secretin effective to stimulate secretion of the pancreatic juices.

3. The method of claim 2 wherein said effective amount of secretin is administered by infusion.

4. The method of claim 3 wherein administering said effective amount of secretin by infusion includes the step of intravenously infusing secretin in an amount of about 2 clinical units (CU) per kilogram (kg) of body weight.

5. The method of claim 4 wherein said effective amount of secretin is administered transdermally.

6. The method of claim 5 wherein administering said effective amount of secretin transdermally includes the steps of:

applying a transdermal carrier to a portion of the skin of said patient; and applying crystalline secretin in said effective amount onto said transdermal carrier.

7. The method of claim 6 wherein said transdermal carrier includes dimethyl sulfoxide (DMSO).

8. The method of claim 6 wherein said effective amount of secretin includes between 5 and 20 clinical units (CU) of crystalline secretin per dose.

9. The method of claim 6 wherein said transdermal carrier is selected from the group consisting of a gel and a lotion.

10. The method of claim 5 wherein administering secretin transdermally includes administering said effective amount of secretin with a patch to be applied to a portion of the skin of said patient.

11. The method of claim 2 wherein said effective amount of secretin is administered orally.

12. The method of claim 11 wherein said effective amount of secretin is administered orally using an oral carrier selected from the group consisting of a tablet, capsule or lozenge.

13. The method of claim 2 wherein said effective amount of secretin is administered using a suppository.

14. The method of claim 2 wherein said effective amount of secretin is administered by inhalation.

15. The method of claim 2 wherein said patient suffers from autistic disorder or pervasive development disorder.

16. The method of claim 2 wherein said effective amount of secretin includes an amount of secretin sufficient to increase serotonin levels in the brain of said patient to a level effective to stimulate secretion of the pancreatic juices.

17. The method of claim 1 wherein stimulating secretion of said pancreatic juices increases at least one neuropeptide hormone selected from the group consisting of serotonin, dopamine and CCK levels in said patient.

18. A method for the treatment of autism comprising the step of administering to said patient an effective amount of secretin.

19. The method of claim 18 wherein said effective amount of secretin is administered by infusion.

20. The method of claim 19 wherein administering said effective amount of secretin by infusion includes the step of intravenously transfusing secretin in an amount of about 2 clinical units (CU) per kilogram (kg) of body weight per dose.

21. The method 18 wherein said effective amount of secretin is administered transdermally.

22. The method of claim 21 wherein administering said effective amount of secretin transdermally includes the steps of applying a transdermal carrier to a portion of the skin of said patient; and applying crystalline secretin in said effective amount onto said transdermal carrier.

23. The method of claim 22 wherein said transdermal carrier includes dimethyl sulfoxide (DMSO).

24. The method of claim 23 wherein said effective amount of secretin includes about 15 clinical units (CU) of crystalline secretin per dose.

* * * * *